United States Patent [19]

Kiyoto et al.

[11] Patent Number: 4,670,259

[45] Date of Patent: Jun. 2, 1987

[54] COMPOUND FR-68504, PRODUCTION THEREOF AND USE THEREOF

[75] Inventors: Sumio Kiyoto, Ibaraki; Hidetsugu Murai; Yasuhisa Tsurumi, both of Osaka; Hiroshi Terano, Ibaraki; Masanobu Kohsaka, Sakai, all of Japan

[73] Assignee: Fujisawa Pharmaceutical Co., Ltd., Osaka, Japan

[21] Appl. No.: 813,065

[22] Filed: Dec. 24, 1985

[30] Foreign Application Priority Data

Jan. 2, 1985 [GB] United Kingdom ................ 8500039

[51] Int. Cl.$^4$ .................... A61K 35/70; A61K 35/72; C12P 1/02
[52] U.S. Cl. .................................... 424/118; 435/171
[58] Field of Search ......................... 424/118; 435/171

Primary Examiner—Jerome D. Goldberg
Attorney, Agent, or Firm—Oblon, Fisher, Spivak, McClelland & Maier

[57] ABSTRACT

The invention relates to a new compound, designated FR-68504. The compound has antitimor activities and is effective in the treatment of various tumors in both human beings and animals.

There is also provided a process for preparing FR-68504 compound which comprises culturing a FR-68504 producing strain belonging to the genus *Amauroascus* in a nutrient medium.

Pharmaceutical composition comprising FR-68504 as an active ingredient is also described.

4 Claims, No Drawings

COMPOUND FR-68504, PRODUCTION THEREOF AND USE THEREOF

This invention relates to a new compound FR-68504. More particularly, it relates to a new compound FR-68504 which has activity with respect to lymphocytic leukemia P388, melanotic melanoma B16 and lymphoid leukemia L1210, to a process for producing FR-68504 by culturing a FR-68504-producing strain belonging to the genus Amauroascus in a nutrient medium and to a pharmaceutical composition comprising the same.

The FR-68504 obtained in the Example as mentioned below has the following physicochemical properties:
(a) Appearance: Colorless prisms
(b) Melting point: 157°–159° C.
(c) Optical rotation: $[\alpha]_D^{23} = -5.8°$ (C=1.0, $H_2O$)
(d) Molecular weight:
236 [SIMS: m/z 237 (M+1)]
(e) Elemental analysis (%): C 45.65; H 6.62
(f) UV absorption spectrum: End absorption (in $H_2O$)
(g) IR absorption spectrum: $\nu_{max}^{Nujol}$: 3400, 3250, 1300, 1100, 1030, 950, 850 cm$^{-1}$
(h) $^1$H NMR absorption spectrum: ($D_2O$) δppm: 3.94–3.78 (4H, m), 3.57 (1H, dd, J=9.2 and 5.3 Hz), 3.36–3.25 (2H, m), 3.01–2.88 (4H, m)
(i) $^{13}$C NMR absorption spectrum: ($D_2O$) δppm: 71.0 (d), 70.6 (d), 70.4 (d), 69.6 (d), 68.6 (d), 55.1 (d), 53.5 (d), 46.6 (t), 46.5 (t)
(j) Solubility: Soluble: Water; Sparingly soluble: Methanol, ethanol, acetone; Insoluble: Ethyl acetate, chloroform
(k) Color reaction: Positive: Molish's reaction, reaction with cerium sulfate; Negative: Ninhydrin reaction, ferric chloride-potassium ferricyanide reaction, reaction with Dragendorff reagent or iodine vapor.
(l) Property of substance: Neutral substance
(m) Thin layer chromatography (silica gel sheet):

| Solvent | Rf value |
| --- | --- |
| Chloroform:isopropanol:water (5:10:1) | 0.50 |
| Isopropanol:water (85:15) | 0.70 |

The FR-68504 can be prepared by culturing a FR-68504-producing strain belonging to the genus Amauroascus such as *Amauroascus aureus* F-3405 and the like in a nutrient medium and recovering the FR-68504 from the cultured broth. Among a FR-68504-producing strain belonging to the genus Amauroascus, *Amauroascus aureus* F-3405 was newly isolated from a soil sample collected at the foot of Mt. Mitoku, Tottori Prefecture, Japan by the present inventors. A lyophilized sample of the newly isolated *Amauroascus aureus* F-3405 was deposited with Fermentation Research Institute, Agency of Industrial Science and Technology, Yatabe-cho higashi No. 1-1-3, Tsukuba-gun, Ibaraki-ken, Japan, under the number FERMP-8008 on Dec. 15, 1984 and this deposit was converted to meet the requirement of the Budapest Treaty under the number FERMBP-946 on Dec. 11, 1985.

It is to be understood that the production of the new compound, FR-68504 is not limited to the use of the particular organism described herein, which is given for illustrative purpose only. This invention also includes the use of any mutants which are capable of producing the FR-68504 including natural mutants as well as artificial mutants which can be produced from the described organism by conventional means, such as X-rays, ultra-violet radiation, treatment with N-methyl-N'-nitro-N-nitrosoguanidine, 2-aminopurine and the like.

*Amauroascus aureus* F-3405 has the following morphological, cultural and physiological characteristics.

The ascomata developed on corn meal agar or YpSs agar after one month, and the hyphal conidiomata were observed on various culture media. The conidiogenesis is holoarthric.

The ascomata are superficial, globose or subglobose, yellow and 500–1000 μm in diameter. They are often aggregated and formed to stroma-like masses more than 3000 μm in diameter. The peridium consists of the interwoven hyphae, whose tips are sinurate or spiral. The asci bear irregularly in the ascomata and develop on firmly coiled gametangia in clusters. They are unitunicate, evanescent, eight-spored, obovoid to pyriform with a short stalk, 13–15.5 μm long and 9–10 μm thick. The ascospores are unicellular, yellow, echinulate but finally reticulate, globose and 4–5 μm diameter. The arthroconidia are produced at the tips or in intercalary positions of vegetative hyphae. They are unicellular, hyaline, smooth, cylindrical or ovoid with the truncate base, 8–18 μm long and 4–6 μm. The vegetative hyphae are septate, hyaline, smooth and branched. The hyphal cells are cylindrical and 1.5–5 μm thick. The chlamydospores are absent.

Colonies on malt extract agar grow rather rapidly, attaining 3.5 cm in diameter after 2 weeks at 25° C. The colony surface is plane or slightly raised, felty to floccose, and pale yellow. Neither ascomata nor conidiocose are observed. The reverse is yellow to dark yellow. Colonies on YpSs agar are similar to those on malt extract agar in rate of growth. The surface is plane, felty and pale yellow to yellowish gray. The reverse is pale yellow. The ascomata are formed on this medium after one month at 25° C. Cultures on corn meal agar grow to 2.0 cm in diameter under the same conditions. They are plane, thin, felty and pale yellow. At the center of them many ascomata are formed, and the ascospores mature after 3 to 4 weeks.

The strain F-3405 can grow at the temperature in the range from 5° to 29° C. with the growth optimum at 23° to 26° C. These temperatural data were determined using a temperature gradient incubator (Toyo Kagaku Sangyo Co., Ltd.) on potato dextrose agar. This strain can grow at pH 3 to 10, and has a growth optimum at pH 5 to 7 in YM broth medium (Difco).

On the basis of the morphological characteristics of the strain F-3405, the strain appears to belong to the ascomycete genus Amauroascus Schröter.

According to the taxonomic criteria of the genus Amouroascus, the strain F-3405 was considered to belong to *Amauroascus aureus* (Eidam) von Arx, based on the similarity with respect to ascomata size, in addition to ornamentation, color and size of ascospores. And the above characteristics corresponds with the descriptions of Kuehn et al. (1964) (Cf, *Persoonia*, 6(3), 371–380), von Arx (1971) (Cf. *Mycologia*, 56, 863–872) and Udagawa (1978) (Cf. Kinrui Zukan P388 published by Kodan-sha, Tokyo, Japan) except that the strain F-3405 didn't form the typical Chrysosporium conidial state reported by Kuehn et al. Consequently the strain F-3405 was identified as a new strain of *Amauroascus aureus*, and named to *Amauroascus aureus* F-3405.

In general, FR-68504 can be produced by culturing a FR-68504 producing strain in a nutrient medium containing assimilable sources of carbon and of nitrogen, preferably under aerobic conditions (e.g. shaking culture, submerged culture, etc.).

The preferred sources of carbon in the nutrient medium are carbohydrate such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium iodide, magnesium salt, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the FR-68504. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the rocess of production of the FR-68504. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the FR-68504.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 25° C., for a period of 50 hours to 100 hours, which may be varied according to the fermentation conditions and scale.

Thus produced FR-68504 can be recovered from the culture medium by conventional means which are commonly used for the recovery of other fermentation products such as antibiotics.

In general, most of the FR-68504 produced are found in the culture filtrate, and accordingly FR-68504 can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

Some biological properties of FR-68504 are illustrated in detail in the following tests.

Test 1 (Antitumor activity against lymphocytic leukemia)

The antitumor activity of FR-68504 was determined in experimental tumor system in mice.

Lymphocytic leukemia P388 was implanted intraperitoneally into BDF$_1$ mice (female, 7 weeks aged) at an inoculum size of $1 \times 10^6$ cells per mouse. Twenty-four hours after the implantation of tumor cells, graded doses of FR-68504 in physiological saline were intraperitoneally administered to mice. Treatments of FR-68504 were once a day on day 1, 2 and 3 after tumor inoculation. Control animals were intraperitoneally administered only physiological saline. The injection volume was 0.2 ml in all experiments. Five mice were used for each experimental group.

Antitumor activity was evaluated by the mean survival time of a group of mice and also expressed by the T/C % value (mean survival time of treated group/mean survival time of control, $\times 100$).

The result is shown in Table 1. FR-68504 was considerably active against the leukemia P388.

TABLE 1

| Antitumor activity of FR-68504 | | | |
|---|---|---|---|
| Drug | Dose (mg/kg/day) | Mean survival time (days) | T/C (%) |
| FR-68504 | 16 | 25.5 | 214 |
|  | 8 | 22.3 | 187 |
|  | 4 | 17.7 | 149 |
|  | 2 | 15.9 | 134 |
| Control | — | 11.9 | 100 |

TEST 2 (Antitumor activity against melanotic melanoma)

The antitumor activity of FR-68504 was determined in experimental tumor system in mice.

Melanotic melanoma B16 was implanted intraperitoneally in 8 weeks old, female BDF$_1$ mice at inoculum size of $1 \times 10^6$ cells per mouse. Twenty-four hours after the implantation of tumor cells, a solution of FR-68504 in sterilized water was intraperitoneally administered to mice. The treatments were conducted once a day for 4 days. In this test, five mice were used for each experimental group. Control animals received intraperitoneal doses of only physiological saline solution. The injection volume was 0.2 ml in all experiments.

Antitumor activity was evaluated by the mean survival times of a group of mice and also expressed by the T/C % value.

The result is shown in Table 2. FR-68504 was considerably active against the melanotic melanoma B16.

TABLE 2

| Drug | Dose (mg/kg/day) | Mean Survival time (days) | T/C % |
|---|---|---|---|
| FR-68504 | 10 | 39.1 | 184 |
|  | 5 | 38.0 | 178 |
|  | 2.5 | 29.5 | 138 |
|  | 1.25 | 27.8 | 130 |

TABLE 2-continued

| Drug | Dose (mg/kg/day) | Mean Survival time (days) | T/C % |
|---|---|---|---|
| Control | — | 21.3 | 100 |

Test 3 (Antitumor activity against lymphoid leukemia)

The antitumor activity of FR-68504 was determined in experimental tumor system in mice.

Lymphoid leukemia L1210 were implanted intraperitoneally in 8 weeks old, female, BDF$_1$ mice at inoculum size of $1 \times 10^6$ cells per mouse. Twenty-four hours after the implantation of tumor cells, a solution of FR-68504 in sterilized water was intraperitoneally administered to mice. The treatments were conducted once a day for 4 days. In this test, five mice were used for each experimental group. Control animals received intraperitoneal doses of only physiological saline solution. The injection volume was 0.2 ml in all experiments.

Antitumor activity was evaluated by the mean survival times of a group of mice and also expressed by the T/C % value.

The result is shown in Table 3. FR-68504 was considerably active against the lymphoid leukemia L1210.

TABLE 3

| Drug | Dose (mg/kg/day) | Mean Survival time (days) | T/C % |
|---|---|---|---|
| FR-68504 | 10 | 13.7 | 155 |
| Control | — | 8.6 | 100 |

Test 4 (Antitumor activity against lung carcinoma)

The antitumor activity of FR-68504 was determined in experimental tumor system in mice.

Lewis lung carcinoma were implanted subcutaneously in 8 weeks old, female, BDF$_1$ mice at inoculum size of $2.5 \times 10^6$ cells per mouse. Twenty-four hours after the implantation of tumor cells, a solution of FR-68504 in sterilized water was intraperitoneally administered to mice. The treatments were conducted once a day for 4 days. In this test, five mice were used for each experimental group. Control animals received intraperitoneal doses of only physiological saline solution. The injection volume was 0.2 ml in all experiments.

Antitumor activity was evaluated by the mean survival times of a group of mice and also expressed by the T/C % value.

The result is shown in Table 4. FR-68504 was considerably active against the Lewis lung carcinoma.

TABLE 4

| Drug | Dose (mg/kg/day) | Mean Survival time (days) | T/C % |
|---|---|---|---|
| FR-68504 | 6.0 | 32.5 | 160 |
|  | 1.0 | 27.1 | 133 |
| Control | — | 20.3 | 100 |

Test 5 (Acute toxicity of FR-68504)

LD 50 value of FR-68504 from the result of the acute toxicity test using ddY mice (male, 5 weeks aged) by intraperitoneal injection was 50 mg/kg.

The FR-68504 of this invention in admixture with pharmaceutically acceptable carriers can orally or parenterally be administered as agent with respect to lymphocytic leukemia P388, melanotic melanoma B16 and lymphoid leukemia L1210 to mammals in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. surface active agent, etc.], aqueous diluting agent (e.g. water), oils (e.g. sesame oil, etc.), base wax (e.g. cacao butter, polyethyleneglycol, white petrolatum, etc.).

A dosage of the object compounds are to be varied depending on various factors such as kind of diseases, weight and/or age of a mammalian subject, and further the kind of administration route.

The preferred dosage of FR-68504 is usually selected from a dose range of 0.01–10 mg/kg/day in the case of injection and 0.5–50 mg/kg/day in the case of oral administration.

The following Examples are given for the purpose of illustrating this invention.

EXAMPLE 1

A seed medium (80 ml) containing soluble starch (1%), corn starch (1%), glucose (1%), cotton seed meal (1%), dried yeast (1%), peptone (0.5%), corn steep liquor (0.5%), calcium carbonate (0.2%) (adjusted to pH 6.0 with aqueous sodium hydroxide) was poured into one 250 ml Erlenmeyer flask and sterilized at 120° C. for 30 minutes. A loopful of slant culture of *Amauroascus aureus* F-3405 was inoculated to the medium and cultured at 25° C. for 120 hours on a rotary shaker with 3-inch throw at 200 rpm. Three ml of the resultant culture was inoculated to each of thirty 250 ml Erlenmeyer flasks contained the same seed medium (80 ml), which had been sterilized at 120° C. for 30 minutes in advance, and cultured at 25° C. for 72 hours on the rotary shaker. Two liters of the seed culture were inoculated to the production medium (150 l) containing glucose (2%), peptone (0.5%), dried yeast (1%) and calcium carbonate (0.2%) (adjusted to pH 6.5 with aqueous sodium hydroxide) in a 200 liter-jar fermenter, which had been sterilized at 120° C. for 30 minutes, and cultured at 25° C. for 144 hours under aeration of 150 liters/minutes and agitation of 200 rpm.

The cultured broth thus obtained was filtered with an aid of diatomaceous earth (2 kg). The filtrate (70 l) was adjusted to pH 6.5 with hydrochloric acid and passed through a column packed with an activated carbon (20 l). This column was washed with water (100 l) and eluted with 10% aqueous methanol (80 l). The active eluate was concentrated in vacuo to a volume of 200 ml to yield a precipitate of purified active material which was recrystallized from water-methanol to give FR-68504 (2 g) as colorless prisms.

EXAMPLE 2 (Injection preparation)

Some sterile samples of FR-68504 are distributed into vials, thereby containing 10 mg of the active ingredient. The vials are sealed hermetically to exclude bacteria. Whenever the vials are required for use, 2 ml of sterile distilled water for injection is added to the vial and the vial is subjected to administration.

We claim:

1. A compound, FR-68504 having the following characteristics:
   (a) Elemental analysis (%): C 45.65; H 6.62
   (b) Molecular weight: 236 [SIMS: m/z 237 (M+1)]
   (c) Melting point: 157°-159° C.
   (d) Optical rotation: $[\alpha]_D^{23} = -5.8°$ (C=1.0, $H_2O$)
   (e) UV absorption spectrum: End absorption (in $H_2O$)
   (f) IR absorption spectrum: $\gamma_{max}^{Nujol}$: 3400, 3250, 1300, 1100, 1030, 950, 850 $cm^{-1}$
   (g) $^1H$ NMR absorption spectrum: ($D_2O$) δppm: 3.94-3.78 (4H, m), 3.57 (1H, dd, J=9.2 and 5.3 Hz), 3.36-3.25 (2H, m), 3.01-2.88 (4H, m)
   (h) $^{13}C$ NMR absorption spectrum: ($D_2O$) δppm: 71.0 (d), 70.6 (d), 70.4 (d), 69.6 (d), 68.6 (d), 55.1 (d), 53.5 (d), 46.6 (t) 46.5 (t)
   (i) Solubility: Soluble: Water; Sparingly soluble: Methanol, ethanol, acetone; Insoluble: Ethyl acetate, chloroform
   (j) Color reaction: Positive: Molish's reaction, reaction with cerium sulfate; Negative: Ninhydrin reaction, ferric chloride-potassium ferricyanide reaction, reaction with Dragendorff reagent or iodine vapor
   (k) Property of substance: Neutral substance 2. A process for the production of the compound FR-68504 of claim 1 which comprises culturing *Amauroascus aureus* F-3405 (FERM BP-946) under aerobic conditions in a nutrient medium until a substantial amount of antibiotic activity is imparted to said culture.

3. A pharmaceutical composition for treating lymphocytic leukemia P388, melanotic melanoma B16, or lymphoid leukemia L1210 comprising an effective amount of the compound FR-68504 of claim 1 in admixture with a pharmaceutically acceptable carrier, said effective amount being a dosage of 0.01-10 mg/kg/day by injection or 0.5-50 mg/kg/day by oral administration.

4. A method of treating lymphocytic leukemia P388, melanotic melanoma B16, or lymphoid leukemia L1210, which comprises administering to a mammal in need of such treatment an effective amount of the compound FR-68504 of claim 1, said effective amount being a dosage of 0.01-10 mg/kg/day by injection or 0.5-50 mg/kg/day by oral administration.

* * * * *